United States Patent [19]
Drevin et al.

[11] Patent Number: 5,252,462
[45] Date of Patent: Oct. 12, 1993

[54] ENZYME ACTIVITY DETERMINATIONS METHOD CHARACTERIZED BY THE USING OF SUBSTRATES WHOSE FLUORESCENT PROPERTIES DIFFERS THOSE OF THE CONVERTED PRODUCTS

[75] Inventors: Hakan Drevin; Anna T. Martin; Jan Carlsson, all of Uppsala; Sven O. Oscarsson, Orbyhus, all of Sweden; Timo Lovgren; Ilkka Hemmila, both of Turku, Finland; Marek Kwiatkowski, Uppsala, Sweden

[73] Assignees: Pharmacia AB, Uppsala, Sweden; Wallac OY, Abo, Finland

[21] Appl. No.: 457,691

[22] PCT Filed: Apr. 28, 1989

[86] PCT No.: PCT/SE89/00241
§ 371 Date: Jan. 5, 1990
§ 102(e) Date: Jan. 5, 1990

[87] PCT Pub. No.: WO89/10975
PCT Pub. Date: Nov. 16, 1989

[30] Foreign Application Priority Data
May 5, 1988 [SE] Sweden ............................ 8801702-5

[51] Int. Cl.$^5$ .............................................. C12Q 1/34
[52] U.S. Cl. ..................... 435/018; 435/7.72; 435/968; 436/546; 436/800; 424/7.1
[58] Field of Search ................... 435/18, 7.72, 968; 436/546, 800; 424/7.1

[56] References Cited

U.S. PATENT DOCUMENTS

| | | | |
|---|---|---|---|
| 4,837,169 | 6/1989 | Toner | 435/546 |
| 4,857,475 | 8/1989 | Dakubu | 436/546 |
| 5,011,910 | 4/1991 | Marshall et al. | 530/329 |

FOREIGN PATENT DOCUMENTS

| | | |
|---|---|---|
| A30068875 | 5/1983 | European Pat. Off. |
| 103558 | 3/1984 | European Pat. Off. |
| 324323 | 7/1989 | European Pat. Off. |

*Primary Examiner*—Ronald W. Griffin
*Assistant Examiner*—Pamela S. Webber
*Attorney, Agent, or Firm*—Lowe, Price, LeBlanc & Becker

[57] ABSTRACT

The method for demonstrating the presence of an activity of an enzyme by
(a) incubating said enzyme with a fluorogenic substrate A which is converted by the enzyme to a product B differing from A in respect to its fluorescent properties, A and/or B carrying a chromophore which is a triplet sensitizer having a triplet energy level above the excitation energy level of a lanthanide ion selected from the group consisting of $Eu^{3+}$, $Tb^{3+}$, $Dy^{3+}$ and $Sm^{3+}$ and which is capable of chelating said lanthanide ion by means of an oxygen or nitrogen atom in said chromophore, and that B differs from A either by
(i) carrying a different chromophore, or
(ii) having a different chelating ability, and
(b) measuring the change in fluorescence caused by said enzyme.

9 Claims, No Drawings

ENZYME ACTIVITY DETERMINATIONS METHOD CHARACTERIZED BY THE USING OF SUBSTRATES WHOSE FLUORESCENT PROPERTIES DIFFERS THOSE OF THE CONVERTED PRODUCTS

The technical field of the invention comprises the use of certain specific fluorescent or fluorogenic substrates for enzyme activity measurements.

A fluorescent organic substance usually carries a chromophore i.e. a structure strongly absorbing light of the UV or visible regions. The term "chromophore" therefore refers to a system of double and/or triple bonds which are conjugated with each other or are linked to bridges consisting of hetero atoms with free electrons (in the first place oxygen, nitrogen, sulfur) and hetero atoms bound directly to the system. Often the double bonds will form aromatic ring systems. Changes in the number of double and triple bonds, their relative positions with respect to each other, and the hetero atom binding conditions will strongly affect the light absorbent properties. The effects of groups bound aliphatically are much weaker, and such groups are therefore not regarded as being parts of chromophores.

The rate and course of an enzymatic reaction are determined by the enzyme and the substrate and by a number of other substances which are either required in order for enzyme activity to occur or are apt to strongly influence that activity. Examples of such substances are cofactors like coenzymes and cosubstrates, allosteric effectors and inhibitors. For cases where a sample is suspected to contain one or more of these substances techniques have been developed where the particular substance(s) suspected to be present is/are detected by addition of the remaining substances and measurement of enzyme activity. For clinical samples, various types of enzyme activity have been correlated with specific disorders. Within the field of immunochemical analyses, assays for an analyte with the aid of one or more immune reactants carrying analytically detectable groups have been carried out by using marker groups consisting of some of such substances affecting the course of the enzymatic reaction, including also the enzyme itself.

Fluorescent and fluorogenic substrates were employed already in early types of enzyme activity determination methods. Their advantages resided in the first place in the low detection limit which is characteristic of fluorescent substances. In one of these cases, the substrate and product had virtually identical fluorescent properties; in order to enable substrate conversion to be measured it was necessary to separate the product from the substrate. See for example J. Appl. Biochem. 5 (1983) 399-403 where insoluble casein with covalently bound europium chelate was used for determining the proteolytic activity by means of time resolved fluorescence spectrometry. In the other case a fluorescent or fluorogenic substrate was employed which had fluorescent properties differing from those of the product obtained. This difference could be a difference in excitation as well as a difference in emission characteristics. Basically it was not necessary to separate the substrate from the product. The substrates were constructed in a manner such that the chromophoric structure was formed, destroyed or changed as a consequence of the enzymatic reaction. Both of these types of substrate groups have been synthesized for enzymes belonging to the various different main groups of enzymes (oxidoreductases, transferases, ligases, hydrolases, lyases and osomerases). See e.g. Enzymes; Ed: Dixon, M. et al; Longham Group Ltd, London 1979.

In biological samples fluorescence measurements are thwarted by background fluorescence from e.g. proteins. Due to this background, sensitivity will be found to be low when specific substances are to be determined. It is known that this disturbing effect can be avoided if the fluorescent marker (for example substrate/product) is chosen such that its emission maximum and/or excitation maximum are clearly distinct from the background fluorescence. An alternative approach has been to choose a marker having a long fluorescent decay time as compared to that of the background fluorescence, and to then employ time resolved fluorescence spectrometry for measuring the marker fluorescence. During the recent 10-15 years this last-mentioned alternative has been found to be very suitable for immunochemical techniques using labeled reactants. The marker group in these cases has been a fluorescent lanthanide chelate or a lanthanide chelate which is basically non-fluorescent in itself but has been converted to a fluorescent form. For determining enzyme activity this principle has been employed only once, according to literature sources; and in that case the fluorogenic properties of the substrate and of the product have been identical.

The object of this invention is to improve sensitivity when enzyme activity is measured with the aid of fluorescent/fluorogenic substrates (A) which are converted to a product (B) that has at least one fluorescent/fluorogenic property differing from that of (A).

THE INVENTION

The invention is characterized by employing an entirely new type of pairs of substrate (A)-product (B). In these pairs, (A) and/or (B) has a chromophore which is a triplet sensitizer having a triplet energy level above the energy level of an excited electron in a lanthanide ion selected from among $Eu^{3+}$, $Tb^{3+}$, $Dy^{3+}$, and $Sm^{3+}$ and which is capable of chelating said lanthanide ion by means of an oxygen and/or nitrogen atom present in its structure, optionally together with chelating groups bound to said structure. When an enzymatic reaction occurs this will involve a chemical change, whereby the chelating capacity is either caused to disappear or created and/or the chromophore is caused to undergo a change. Substrate conversion is measured as the fluorescence obtained in the presence of the lanthanide ion, by means of time resolved fluorescence spectrometry. The relative positions of the energy levels in relation to each other will determine whether a long half-life fluorescence is obtained; see for instance Abusaleh, A. and Meares, C. F., Photochem. Photobiol 39 (1984) 763.

CHOOSING THE SUBSTRATE

When choosing his substrate, the man skilled in the art may be guided by considerations as to which particular enzyme activity is to be determined and by his knowledge of chromophores suitable for time resolved fluorescence spectroscopy. Known rules are applied. In view of the keen interest focused during these last 10-15 years on time resolved fluorescence spectroscopy with the aid of lanthanide chelates, the basic structural requirements to be fulfilled by such chelates are now known. Various different compounds have been synthesized. It is imperative for at least one of the ligands of the chelator ("donor atoms", always a hetero atom) to be present in the chromophore in order to ensure an efficient energy transfer between the light absorbing unit and the light emitting lanthanide ion. In order for the chelation to be favored thermodynamically the compound has to comprise a plurality of hetero atoms which are capable, jointly and together with at least one chromophore hetero atom, of coordinating (chelating) a given shared lanthanide ion so as to form 5- or 6-membered rings in which the lanthanide ion is a common link. This condition, which is a basic requirement for obtaining chelation, means that the bridge linking two chelating hetero atoms together consists of three or, preferably, two atoms.

The chromophores hitherto employed in the context of time resolved fluorescence spectroscopy have comprised an aromatic ring system, this system being optionally condensed and/or being heteroaromatic containing oxygen and/or nitrogen and/or sulfur. In addition to the hetero atom(s) and aromatic rings coordinating a lanthanide ion the chromophore has contained further hetero atoms, aromatic rings and double and triple bonds. Examples of specific structures are pyridine with substituted alkynyl groups in the 3-, 4- or 5-positions and with chelating groups in the 2- and 6-positions; 9,10-phenanthrolines similaryl provided with chelating groups; 2,2'-bipyridines; 2,2'-bipyrimidines; 2,2'-bipyrimidazines; and corresponding structures having a bridge between their rings to permit the ring nitrogens to jointly coordinate shared lanthanide ion; aromatic beta-diketones; phenolic groupings provided with chelating groups etc.

When the known compounds to be used as markers in time resolved fluorescence spectroscopy were being synthesized the possibility that they might form enzyme substrates was not considered at all. This is why they can only in very exceptional cases be used directly in the method of the present invention. An important point when the substrate is to be chosen is to make sure that the structural demands dictated by the nature of the enzyme are really fulfilled and that the conversion of substrate to product will bring about a change in the fluorogenic/fluorophoric properties, either directly or in that the product formed participates in further reactions (e.g. rearrangements) to form a more suitable product. For enzymes having an activity directed against heteroatom-containing structures it is possible to utilize hetero atoms present in the chromophore. Depending on the type of enzyme to be employed, one of the hetero atoms of the chromophore may be present in the form of an amine, amide, alcohol, phenol, carbonyl, ester, phosphate esters, phosphonate, phosphate, carboxylic acid, sulfonate, sulfate, enolate, ether etc. and then under the action of the enzyme undergo a change in respect of its bonding. Specificity for the target enzyme is obtained by means of coupling additional groups to the hetero atom employed. In principle, it is possible to produce substrates for all the six main groups of enzymes.

Alternatively, the substrate/product may be derivatized at a chelating hetero atom that does not form part of the chromophore. In the case of this alternative the derivatization has to be such that the enzyme will accomplish a total change of chelating ability—either so that the substrate does not have this ability while the product does, or vice versa. The construction of a substrate for a given enzyme is performed according to known rules.

For the determination of enzyme activity which causes the binding conditions in a chromophore to undergo a change the substrates most commonly employed may be assigned the general formula $$F-Y-X$$

where X and Y form the chromophore with the aforesaid chelating groups, Y is an enzymatically cleavable group of the type mentioned hereinbefore, and F is a structure tailored in a manner such that the substrate will fit a given enzyme. For hydrolases, groups X and Y will be chosen in the first place so that an aromatic amine or an OH group bound to a conjugated system (as e.g. phenol) is either formed or destroyed as a consequence of the enzymatic reaction, with a concomitant change in fluorescence. As examples of pairs of enzyme—substrate may be mentioned the following:

| Enzyme | X Y F |
|---|---|
| aminoacyl transpeptidase | X—NHOC-amino acid |
| protease, peptidase | X—NHOC—CRNH-peptide |
| glycosidase (glycoside linkage) | X—O-sugar |
| phosphatase | X—O-phosphate |
| esterase | X—O-acyl |

In the experimental portion of the invention pairs of substrate—product are set forth in which the chelating capacity as well as the chromophore is affected by the enzyme.

Carrying out the invention in actual practice

In accordance with the invention, samples and enzyme substrates are incubated together with standardized amounts of the remaining substances which are required for the reaction and are not to be determined. In cases where the pH values of the samples are liable to vary, buffer systems are added which have a capacity great enough to compensate for such variation. The optimum pH conditions will vary with the enzyme, but will normally be within the range of from 3 to 10. A temperature is chosen within the range of 0°–40° C., preferably at a pH at which activity is at a maximum. As regards accuracy and sensitivity, these will both be best if the pH and temperature are chosen within ranges in which the reaction is independent of these variables.

According to one embodiment of the invention, the marker systems employed are enzymatic reactions with the above-described substrates in immunochemical assay and other methods involving biospecific affinity reactions. For the sake of simplicity, these methods will be described as immunochemical methods. This is feasible because fundamentally they are very similar. Examples of other biospecific affinity reactions are those between complementary nucleic acids (DNA, RNA), lectin—carbohydrate, protein A—$F_c$-IgG etc.

In immunochemical assay methods for determining an analyte with the aid of a labeled immune reactant, the labeled reactant is caused to immunochemically react with its immunological counterpart so that an immune complex containing both of them is formed in an amount depending on the amount of the analyte. The next step then consists in determining either the amount of labeled reactant incorporated in the complex or the amount thereof which has not been incorporated in the complex. The reaction conditions—like e.g. the particular types of immune reactants and additives to be chosen, the sequence of additions, temperature, pH etc.—are all well known to persons skilled in the art. If the activity of the marker group is subject to a change due to its incorporation in the immune complex it is not necessary to physically separate the complex from the uncomplexed labeled reactant. Such methods are referred to as "homogeneous methods". If a separation is performed the methods are referred to as being "heterogeneous". In some cases, the methods are called "competitive", the analyte being in these cases made to compete with an analyte analog (analyte either labeled or bound to a phase that is insoluble in the reaction medium) for an insufficient amount of an immunochemical counterpart that is common to both of them. In other cases, the methods are said to be "non-competitive"; for example methods in which a given analyte is made to react with an excess of two immunological counterparts which are capable of simultaneously binding to different epitopes on the analyte. What is obtained in this latter case is a ternary complex which may then be detected (sandwich methods). Immunochemical reactions are usually carried out at a pH within the range of 5–9 at a temperature within the range of 0°–40° C. For nucleic acid hybridizations higher temperatures and more extreme pH values may be required. The optimum values are determined by means of simple tests and will depend inter alia on the antibody and antigen employed. In the context of this type of immunochemical tests, the term "enzymatically active group" is to be construed as referring to any and all groups participating in or affecting the course of an enzymatic reaction.

The invention is defined more closely in the attached claims which constitute a part of this specification. The invention will now be further illustrated by way of patent examples.

EXAMPLE 1

4-(2-naphthyl)-4-(2,3,4,6-tetraacetylgalactopyranosyloxy)-1,1,1-trifluoro-3-buten-2-one and
4-(2-naphthyl)-2-(2,3,4,6-tetraacetylgalactopyranosyloxy)-1,1,1-trifluoro-2-buten-4-one 5 g (10 mmol) tetrabutylammonium 3-(2-naphthoyl)-1,1,1-trifluoroacetonate were produced in that 10.5 g of 4-(2-naphthyl)-1,1,1-trifluoro-2,4-butanedione (produced according to J. C. Reid and M. Calvin, *J. Amer. Chem. Soc.* 72 (1950) 2948-2952) were reacted with 4.4 g of sodium hydroxide dissolved in 50 ml of cold water and 5.5 g of tetrabutyl ammonium hydrogen sulfate in 50 ml of chloroform. The solutions were vigorously mixed and the chloroform phase was recovered.

The product was recrystallized in actone. $^1$H NMR (DMSO-$d_6$): 8.2 (1H, s), 7.9 (4H, m), 7.5 (2H, m), 5.76 (1H, s), 3.15 (8H, t), 1.55 (8H, m), 1.36 (8H, m), 0.92 (12H, t).

The product from the above step was dissolved in 50 ml of dry acetone, whereupon 4.1 g (10 mmol) of 2,3,4,6-tetraacetylgalactopyranosyl bromide dissolved in 50 ml of dry acetone were added slowly and dropwise. A precipitate was formed, and the reaction mixture was left standing overnight. The precipitate was filtered off; it consisted of tetrabutyl ammonium bromide. The residual solution was flash chromatographed in toluene/ethanol to thus give the desired product in a yield of 4.25 g (71 %). $^1$H NMR confirmed that the desired product had been obtained.

TLC (silica gel), $R_f$=0.42 in toluene:methanol 4:1 (beta-diketone $R_f$=0.87, Q salt $R_f$=0).

$^1$H NMR (DMSO-$d_6$): 8.6 (1H, s), 8.2-7.2 (m), 6.4 (1H, d, J=10.8 Hz), 5.9 (1H, m), 5.5-5.0 (2H, m), 4.0 (2H, d), 2.1 (3H, s), 2.0 (3H, s), 2.0 (3H, s), 1.9 (3H, s).

EXAMPLE 2

4-(2-naphthyl)-4-galactopyranosyloxy-1,1,1-trifluoro-3-buten-2-one and
4-(2-naphthyl)-2-galactopyranosyloxy-1,1,1-trifluoro-2-buten-4-one (substrate 1)

1 g of chromatographed product from Example 1 was hydrolyzed in 20 ml of 2M sodium methoxide in methanol for 6 hours at 2°-8° C., whereupon the methanol was evaporated and diethyl ether was added. The ethereal phase was extracted with water, pH 1, dried with sodium sulfate and evaporated. According to NMR analysis, 30% of the crude product consists of the desired enol ethers.

$^1$H NMR (DMSO-$d_6$) 8.43 (1H, s), 7.8 (4H, m), 7.5 (2H, m), 6.6 (1H, s), 5.1 (1H, m), 3.4 (5H, m).

EXAMPLE 3

4-(2,3,4,6-tetraacetylgalactopyranosyloxy)-4-(2-thienyl)-1,1,1-trifluoro-3-buten-2-one and
2-(2,3,4,6-tetraacetylgalactopyranosyloxy)-4-(2-thienyl)-1,1,1-trifluoro-2-buten-4-one Tetrabutylammonium thenoyl trifluoroacetonate was produced in that 17 g (0.05 mol) of tetrabutyl ammonium hydrogen sulfate were added to a cooled solution of 4.4 g of sodium hydroxide in 50 ml of water. This was followed by an addition of 11.1 g of 4,4,4-trifluoro-1-(2-thienyl)-1,3-butanedione (Merck), the solution then being extracted with 50 ml of chloroform. The chloroform phase was dried with Na$_2$SO$_4$ and evaporated. Needle crystals were formed and were recrystallized in acetone. The yield amounted to 6.1 g (26%).

$^1$H NMR (DMSO-$d_6$): 7.52 (1H, dd), 7.28 (1H, dd), 6.98 (1H, dd), 5.88 (1H, s), 3.24 (8H, dd, J=9.8 Hz), 1.52 (8H, dq, J=6.8 Hz), 1.36 (8H, dq J=6.8 Hz), 0.95 (12H, t, J=6.8).

2.2 g (5 mmol) of tetrabutyl ammonium thenoyl trifluoroacetonate were dissolved in 50 ml of dry acetone, whereupon 2.05 g (3 mmol) of 2,3,4,6-tetraacetyl-alpha-d-galactopyranosyl bromide (Sigma) were added. After 6 hours the colour of the solution became weakly yellow and a precipitate had formed. TLC (toluene:methanol 4:1) showed one more spot in addition to that of the starting material. The acetone solution was evaporated. The residue was dissolved in chloroform which was extracted with water (pH 5). The chloroform phase was dried with Na$_2$SO$_4$ and evaporated. An oil was obtained as the residue, and when isopropanol was added tetrabutyl ammonium bromide precipitated. The residue—1.4 g of a yellow oil—was flash chromatographed (toluene:methanol), and a fraction containing the desired product had the following NMR spectrum:

$^1$H NMR (DMSO-$d_6$): 8.0 (1H, m), 7.65 (1H, d, J=4.4 Hz), 7.2 (2H, m+s), 6.08 (1H, d, J=3.4 Hz), 5.51 (1H, d, J=6.3 Hz), 5.25 (1H, d, J=3.4 Hz), 5.0 (1H, dd), 3.3 (1H, t, J=6.3 Hz), 3.0 (2H, d, J=6.3 Hz), 2.11 (3H, s), 2.10 (3H, s), 1.99 (3H, s), 1.97 (3H s).

EXAMPLE 4

4-galactopyranosyloxy-4-thienyl-1,1,1-trifluoro-3-buten-2-one and 2-galactopyranosyloxy-4-thienyl-1,1,1-trifluoro-2-buten-4-one (substrate 2)

The product of Example 3 was reacted with 2M sodium methoxide in methanol at 2°-8° C. while being stirred. After 15 hours the methanol solution was evaporated, and the residue was worked up in diethyl ether which was extracted with an acidic aqueous solution. The ether phase contained a deacetylated sugar derivative (desired product) and free beta-diketone.

$^1$H NMR (DMSO-d$_6$): 8.0-7.2 (m), 6.8 (1), 6.4 (1), 5.0 (2H, m), 4.2 (1H, m), 3.6 (1H, m), 3.5 (1H, dt), 3.3 (1H, t, J=2.14 Hz).

EXAMPLE 5

Europium chelate of 4-(4-aminophenylethynyl)2,6-di(N,N-bis(carboxymethyl)-aminomethyl)-pyridine (biotinylated at its 4-aminophenyl group) (substrate 3)

The europium chelate of 4-(4-aminophenylethynyl)-2,6-di(N,N-bis(carboxymethyl)-aminomethyl)-pyridine was synthesized as according to Kankare et al. (EP-A-203047). The chelate was then coupled in the following manner: 10 mg of biotin were reacted with 2 ml of thionyl chloride at room temperature. Excess thionyl chloride was evaporated, and the crystalline biotin acid chloride was dissolved in methylene chloride. The europium chelate of Kankare et al. was dissolved in 1N NaOH, whereupon the biotin acid chloride was added slowly, with vigorous stirring, at 0° C. The reaction mixture was then evaporated to dryness and the biotinylated chelate was purified by TLC (with acetonitrile:water 4:1 as the eluent).

EXAMPLE 6

Fluorescence measurements

Fluorescence measurements were performed with a Perkin Elmer LS-5 Luminescence Spectrometer. The measurements were carried out with an 0.05 ms delay time. A solution of substrate 1 (Example 2) was prepared, with a concentration of 3.2 ng crude product per ml of 0.1M borate buffer, pH 8. The absorbance of the solution thus produced was less than 0.1 at 300-350 nm (Hitachi U-3200 Spectrophotometer). Europium(3+)-chloride ($3 \times 10^{-5}$M) was added to the solution. Due to small amounts of free 4-(2-naphthyl)-1,1,1-trifluoro-2,4-butanedione present in the crude product, fluorescence was obtained with excitation and emission maxima at 338 nm and at 590 and 614 nm respectively. Addition of beta-galactosidase to a concentration of $0.6 \times 10^{-6}$M resulted in an 89-fold increase of intensity at the said emission maxima. This shows that beta-galactosidase will give a product-the increase the fluorescence of the europium ions. When beta-galactosidase was added to a solution containing only europium ions the fluorescence as measured was not affected. If the beta-galactosidase addition was replaced by an addition of urease—an enzyme which has appproximately the same molecular weight as beta-galactosidase but does not cleave the galactosidic linkage—the fluorescence was not altered. In case lactose was present in the substrate solution the galactosidase addition resulted in a slow increase of fluorescence. One hour after the addition of beta-galactosidase the fluorescence had increased by a factor of 10, and after 20 hours by a factor of 206. If no beta-galactosidase was added the fluorescence decreased very slightly during the same period of time. Incremental additions of beta-galactosidase to an 0,1M borate buffer, pH 8, containing 2,6 ng of substrate per ml and $3 \times 10^{-5}$M Eu$^{3+}$ ions, resulted in an increased intensity of the delayed fluorescence. Measurements with substrate 2 from Example 3 were performed in an analogous way. At excitation wavelength 339 nm and emission wavelength 614 nm the intensity was increased 3,7-fold by beta-galactosidase addition.

This experiment shows that fluorescence of a substrate 1 solution is intensified upon addition of beta-galactosidase, that this increase in fluorescence is specific for this enzyme, and that the rate at which the fluorescent product develops is affected negatively by the presence of the natural substrate of beta-galactosidase i.e. lactose.

EXAMPLE 7

Enzyme immunoassay employing time resolved fluorescence spectrometry

Substrate 1, i.e. the product of Example 2, was used as substrate in Pharmacia IgE EIA (Pharmacia, Uppsala, Sweden). This method is a so-called sandwich immunoassay employing beta-galactosidase labelled anti-IgE.

The coated tubes were washed with 2 ml of sodium chloride solution (9 mg/ml). Next, 50 µl of enzyme-antiIgE solution and 50 µl of standard solution containing 0, 2, 5 or 20 kU/1 IgE were added, whereupon the tubes were left to stand, with shaking, for 3 hours at room temperature. The tubes were then washed 3 times with 2 ml of sodium chloride solution (9 mg/ml). This was followed by an addition of 0,5 ml of developer solution consisting of substrate 1 (12 µg/ml) and europium$^{3+}$ chloride ($9 \times 10^{-10}$M), both dissolved in 0,1M borate buffer, pH 7,5. After 30 minutes of incubation at +37° C. the fluorescence of the solution was measured by means of the time-resolved assay technique (fluorometer from Wallac Oy) (Soini, E. and Kojola, H. (1983) Clin. Chem. 29, 65-68). Fluorescence increased with increasing amounts of IgE.

In parallel with the tests described above, the same immunochemical method was carried out but with colorimetric measurement according to the producer's directions. The coated tubes were washed with 2 ml of sodium chloride solution (9 mg/ml) containing Tween ®. This was followed by an addition of 50 µl of enzyme-antiIgE solution and 50 µl of standard solution as described above. The tubes were then shaken for 3 hours, whereupon they were washed 3 times with the sodium chloride solution. This was then followed by an addition of 200 µl of developer solution containing o-nitrophenyl-beta-galactopyranoside. After incubation at 87° C. for 30 minutes 1 ml of sodium carbonate solution (0,60M) was added, and absorbance was measured at 420 nm.

Results obtained with the different substrates could be directly correlated with each other. This experiment demonstrates that the substrate from Example 2 is useful as substrate in an enzyme immunoassay.

EXAMPLE 8

Biotinidase activity detection in serum with the aid of substrate 3 (biotinidase EC 3.5.1.12)

20 µl of untreated serum or 20 µl of heat inactivated serum were incubated with europium labelled biotin (substrate 3 of Example 5, 1-100 nM) in Tris-HCl buffer (50 mM, pH 7,5) containing 0,9 % (w/v) NaCl, 0,5 % (w/v) NaN$_3$ and 0,5 % bovine serum albumin. By means of time resolved fluorescence spectrometry the enzymatic conversion of the substrate was monitored for 13 hours, in the form of a decrease in fluorescence. The substrate thus had a fluorescence stronger than that of the product formed. In the heat inactivated sample, the decrease in fluorescence was about 20 %, whereas in the untreated sample said decrease amounted to about 60%.

EXAMPLE 9

1,3-diphenyl-1-galactopyranosyloxy-propylen-3-one 1,4 g dibenzoylmethane (Aldrich) was suspended in 20 ml dimethylsulfoxide and 0,7 g potassium carbonate was added followed by the addition of 2,9 g 1-bromo-2,3,4,6-tetraacetyl-0-galactose (Sigma) whereafter the solution was stirred for 16 hours. The raw product was then flash chromatographed using silica gel (toluene:-methanol) and a fraction was obtained which had the following NMR spectrum after solvent removal by rotary-evaporation:

$^1$H NMR (DMSO-d$_6$): 8,0 (m, 6H), 7,6 (m, 4H), 6,5 (s, 1H), 4,5-3 (m), 2,5 (s, 12H).

This spectrum confirms that 1,3-diphenyl-(2,3,4,6-tetraacetyl-0-galactopyranosyloxy-propylen-3-one has been formed. This fraction was further treated with 1 equivalent triethylamine in a water and methanol solution (1:1) and, after 24 hours, the solution was evaporated and the residue dried using phosphorus pentoxide under vacuum. The product was diluted with 0,1M sodium borate solution (pH 8) so that the absorbance at 320 nm was ≦0,1. Time resolved fluoroscence was later measured according to Example 6 at T$_d$=0,05 seconds and T$_g$=1 second. When 10 μl 3 mM europium(3+)-chloride solution was added, a fluorescence value of 0,2 at exitation wave length 332 nm and emission wave length 614 nm was obtained. When 1 mg beta-galactosidase (345 units per mg) was added, upon stirring the fluorescence increased to 5,7 after 24 hours. This corresponds to a 28 fold increase. Furthermore, no increase of the fluorescence was seen if no beta-galactosidase was added. This demonstrates that 1,3-dipheny-1-galactopyranosyloxy-propylen-3-one was formed and that enzymatic activity can be measured using time resolved fluorescence.

EXAMPLE 10

Demonstration of time resolved fluorescence using 2-acetyl-3-beta-D-galactopyranosyloxyfuran as a enzyme substrate 2-acetyl-3-beta-D-galactopyranosyloxyfuran was prepared according to J. E. Hodge and E. C. Nelson (Cereal Chemistry (1961) page 207). The product was purified using preparative thin layer chromatography, with "PSC-Fertigplatten kieselgel 60 F$_{254}$S" (Merck) and butanol:water:acetic acid (5:4:1, the organic phase). The band with the rf-value 0,42 was scraped off and the product was extracted with a Soxhlet apparatus using ethanol. The ethanol solution was diluted with 0,1M sodium borate solution (pH 8) so that the absorbance of the solution became ≦0.1 at 309 nm. To this solution, 10 μl 11 mM terbium(3+)chloride was added and the time resolved fluorescence was measured using Perkin Elmer LS-5 Spectrophotometer (T$_d$=0,05 seconds and T$_g$=1 second). When the sample was exitated at 309 nm, the emission maximum was obtained at 540 nm with a fluorescence value of 0,03. When 1,1 mg beta-galactosidase (345 units per mg) was added, the fluorescence increased immediately and after 2 hours a fluorescence value of 0,17 was obtained which means that the fluorescence has increased 5,7 times. Thus 2-acetyl-3-beta-D-galactopyranosyloxyfuran has low fluorescence together with terbium$^{3+}$ ions but when beta-galactosidase was added, the compound functioned as a substrate for the enzyme and a product was formed that, together with terbium$^{3+}$ ions, showed fluorescence.

We claim:

1. In the method for demonstrating the presence of an activity of an enzyme by
   (a) incubating said enzyme with a fluorogenic substrate A which is converted by the enzyme to a product B differing from A in respect to its fluorescent properties and with standardized amounts of remaining substances necessary for the activity, and
   (b) measuring the change in fluorescence caused by said enzyme, the improvement being that at least one of (1) said substrate A and (2) said product B is provided with a chromophore which is a triplet sensitizer having a triple energy level above the excitation energy level of a lanthanide ion selected from the group consisting of Eu$^{3+}$, Tb$^{3+}$, Dy$^{3+}$ and Sm$^{3+}$ and which is can chelate said lanthanide ion by means of an oxygen or nitrogen atom in said chromophore, and that B differs from A either by
   (i) carrying a different chromophore, or
   (ii) having a different chelating activity.

2. The method of claim 1 wherein said substrate A carries said chromophore.

3. The method of claim 1 wherein said product B carries said chromophore.

4. The method according to claim 2 wherein said substrate A in addition to said chelating heteroatom in the chromophore additional contains chelating groups bound to said chromophore.

5. The method according to claim 3 wherein said product B in addition to said chelating heteroatom in the chromophore contains additionally contains chelating groups bound to said chromophore.

6. The method according to claim 1 wherein
   (i) said enzyme is a hydrolase, and
   (ii) said substrate A is a substrate for said hydrolase and
   (iii) said chromophore of said substrate has an oxygen or nitrogen atom that binds to a blocking group that is removed during said incubation thereby transforming said nitrogen or oxygen to an atom that participates in the chelation of said lanthanide ion in said product B.

7. The method according to claim 6 wherein
   (i) said hydrolase is a glycosidase, and
   (ii) said substrate A is a substrate that carries a chromophore having an oxygen atom that forms part of glycoside linkage which is cleaved during said incubation with said glycosidase.

8. The method according to claim 7 wherein said glycosidase is beta-galactosidase and said glycoside linkage being a galactoside linkage.

9. The method according to claim 1 wherein the substrate conversion is carried out in the presence of the lanthanide ion.

* * * * *